United States Patent [19]

Indig et al.

[11] Patent Number: 5,262,038
[45] Date of Patent: Nov. 16, 1993

[54] REFERENCE ELECTRODE PROBE FOR USE IN AQUEOUS ENVIRONMENTS OF HIGH TEMPERATURE

[75] Inventors: Maurice E. Indig; Gary L. Smith, both of Fremont, Calif.

[73] Assignee: General Electric Company, San Jose, Calif.

[21] Appl. No.: 745,292

[22] Filed: Aug. 15, 1991

[51] Int. Cl.$^5$ .............................................. G01N 27/30
[52] U.S. Cl. .................................... 204/435; 204/286; 204/297 R
[58] Field of Search ...................... 204/286, 297 R, 435

[56] References Cited

U.S. PATENT DOCUMENTS

| | | | |
|---|---|---|---|
| 4,290,872 | 9/1981 | Monter et al. | 204/435 |
| 4,636,292 | 1/1987 | Fejas et al. | 204/435 |
| 4,888,102 | 12/1989 | Kessie | 204/435 |
| 4,948,492 | 8/1990 | Niedrach et al. | 204/435 |

OTHER PUBLICATIONS

Agrawal et al, "A Silver–Silver Chloride Reference Electrode for the High Temperature and High Pressure Electrochemistry", *Corrosion*, vol. 33, No. 11, Nov., 1977, pp. 418–419.

*Primary Examiner*—T. Tung
*Attorney, Agent, or Firm*—John S. Beulick

[57] ABSTRACT

Disclosed is a reference electrode probe for employment in monitoring electrochemical potentials. The inventive electrode probe comprises an elongate alumina tube having a closed distal end and a flanged open proximal end, there being at least one hole, and preferably two holes, penetrating through said tube at its closed distal end. An elongate silver electrode coated with silver chloride is housed atactilely within said alumina tube. Zirconia cloth is disposed in the closed distal end of said alumina tube and covers the hole in said alumina tube, and extended up to and may be spaced-apart from said silver electrode. A silver connector is housed atactilely within said alumina tube to its opening, and has a recess at its distal end into which said coated silver electrode is fitted and a threaded recess at its proximal end at the alumina tube opening. An insulated silver alloy rod having a distal end is threaded into the proximal recess of said silver connector. An annular elastomeric seal is in sealing relationship with the open proximal end of said alumina tube and is retaining in its annulus the distal end of said insulated silver alloy rod at its distal end. An elongate annular alumina insulator having a flanged distal end is abutted against the proximal end of said annular seal and retains said insulated silver alloy rod within its annulus. A retainer which retains said insulated silver alloy rod at the proximal end of said annular alumina insulator. Finally, a threaded two-piece annular fitting that retains said probe within its annulus contacts the flange of said alumina tube and the flange of said alumina insulator with a polymeric washer interposed between said flanges and said fitting. Tightening said fitting brings said annular seal into water-tight sealing relationship with the open proximal end of said alumina tube.

15 Claims, 2 Drawing Sheets

REFERENCE ELECTRODE PROBE FOR USE IN AQUEOUS ENVIRONMENTS OF HIGH TEMPERATURE

BACKGROUND OF THE INVENTION

The nuclear power industry long has been engaged in a multitude of studies and investigations seeking improvement in the stamina and reliability of the materials and components forming a reactor based power system. One such investigation has been concerned with intergranular stress corrosion cracking (IGSCC) which heretofore principally has been manifested in the water recirculation piping systems external to the radiation intense reactor core regions of nuclear facilities. Typically, the piping architecture of these external systems is formed of a stainless steel material. Generally, these studies have determined that three factors must occur in coincidence to create IGSCC promotional conditions. These factors are: (a) a sensitization of the metal (stainless steel), for example, such as caused by a chromium depletion at grain boundaries which may be caused by heat treatment in the course of normal processing of the material or by welding and like procedures; (b) the presence of tensile stress in the material; and (c) the oxygenated normal water chemistry (NWC) environment typically present in a boiling water reactor (BWR). This latter environment is occasioned by any of a variety of oxidizing species contributed by impurities in reactor coolant water. By removing any one of these three factors, the IGSCC phenomenon is essentially obviated. Such removal particularly has been accomplished with respect to the latter, oxygenated environment factor through employment of an electrochemical potential monitoring approach combined with an associated hydrogen water chemistry (HWC) technique providing for a controlled addition or injection of hydrogen into the aqueous coolant environment.

Electrochemical potential monitoring is carried out employing paired electrochemical half-cell probes or electrodes which are mounted within the recirculation piping or in an external vessel which has its water source from the reactor water in the recirculation piping. The electrodes are accessed to the external environment through gland type mountings or the like. Where, as in the instant application, the electrode system of interest involves the potential from a metal corrosion electrode, then the reference electrode can conveniently be a metal-insoluble salt electrode, if the metal-salt couple is chemically stable and if appropriate thermodynamic data is available. Accordingly, one of the thus-mounted probes which is configured as a reference electrode may be based, for example, on a silver/silver chloride half-cell reaction. Once the reference electrode half-cell is defined, the cell is completed with the sensing cell portion based upon a metal such as platinum or stainless steel. Verification of the reference electrode and/or the electrode pair is carried out by thermodynamic evaluation and appropriate Nernst based electrochemical calculations in combination with laboratory testing within a known environment.

Half cell electrodes developed for use in reactor circulation piping traditionally have been configured with metal housings, high temperature ceramics, and polymeric seals such as Teflon brand polytetrafluoroethylene. However, most, if not all of these structures, have limited lives, especially in HWC, due to passage of $H_2$ to the active portion of the sensor where chemical and spurious electrochemical reactions occur. Such reactions cause significant voltage shifts. One such prior reference electrode design is set forth in U.S. Pat. Nos. 4,500,413 and 4,576,667. This electrode design, however, has not proven useful in use in BWRs or in high temperature test systems.

BROAD STATEMENT OF THE INVENTION

Disclosed is a reference electrode probe for employment in monitoring electrochemical potentials. The inventive electrode probe comprises an elongate alumina tube having a closed distal end and a flanged open proximal end, there being at least one hole, preferably two holes, penetrating through said tube at its closed distal end. An elongate silver electrode coated with silver chloride is housed atactilely within said alumina tube. Zirconia cloth is disposed in the closed distal end of said alumina tube and covers the hole in said alumina tube, and extended up to but may be spaced-apart from said silver electrode. A silver connector is housed atactiley within said alumina tube to its opening, and has a recess at its distal end into which said coated silver electrode is fitted and a recess at its proximal end at the alumina tube opening. An insulated silver alloy rod having a distal end is fitted into the proximal recess of said silver connector. An annular elastomeric seal is in sealing relationship with the open proximal end of said alumina tube and is retaining in its annulus the distal end of said insulated silver alloy rod. An elongate annular alumina insulator having a flanged distal end is abutted against the proximal end of said annular seal and retains said insulated silver alloy rod within its annulus. A retainer which retains said insulated silver alloy rod at the proximal end of said annular alumina insulator. Finally, a threaded two-piece annular fitting that retains said probe within its annulus contacts the flange of said alumina tube and the flange of said alumina insulator with a polymeric washer interposed between said flanges and said fitting. Tightening said fitting brings said annular seal into water-tight sealing relationship with the open proximal end of said alumina tube.

One advantage of the present invention is a design that utilizes a conventional high temperature sealing gland. Another advantage is an electrode design that is inexpensive, easy to fabricate, yet has an extremely long shelf life. Yet a further advantage is an electrode design that is simple, yet quite accurate. These and other advantages will be readily apparent to those skilled in the art based upon the disclosure contained herein.

The drawings will be described in detail in connection with the following description of the invention.

DETAILED DESCRIPTION OF THE INVENTION

While having utility in a broad variety of industrial monitoring functions, the electrode structure of the instant invention finds particular utility operating under the rigorous environment of the reactor core of a nuclear power facility. The electrode finds preferable employment as a reference component of an electrode system involving a metal-metal ion couple and, thus, the instant electrode can conveniently is a silver-silver chloride reference which functions reversibly. In general, these electrodes may consist of a silver metal with silver chloride immersed in a solution containing chloride anions. In the present design, however, a silver electrode rode is coated with silver chloride. The electrode reaction is:

$$AgCl(s) + e^- \rightarrow Ag(s) + Cl^-$$

At 25° C., the electrochemical chemical potential of such an electrode can be computed as:

$$V(SHE) = 0.2222 - 0.05915 \log 10^a Cl^-,$$

where V(SHE) means the voltage of the electrode of interest versus the standard hydrogen electrode. For a more detailed discussion in connection with the above, reference is made to G.W. Castellan, *Physical Chemistry*, Chapter 17, "Equilibria in Electrochemical Cells", pp 344–382, Addison-Wesley Publishing Co., Reading, Mass. (1964).

Figure 1:
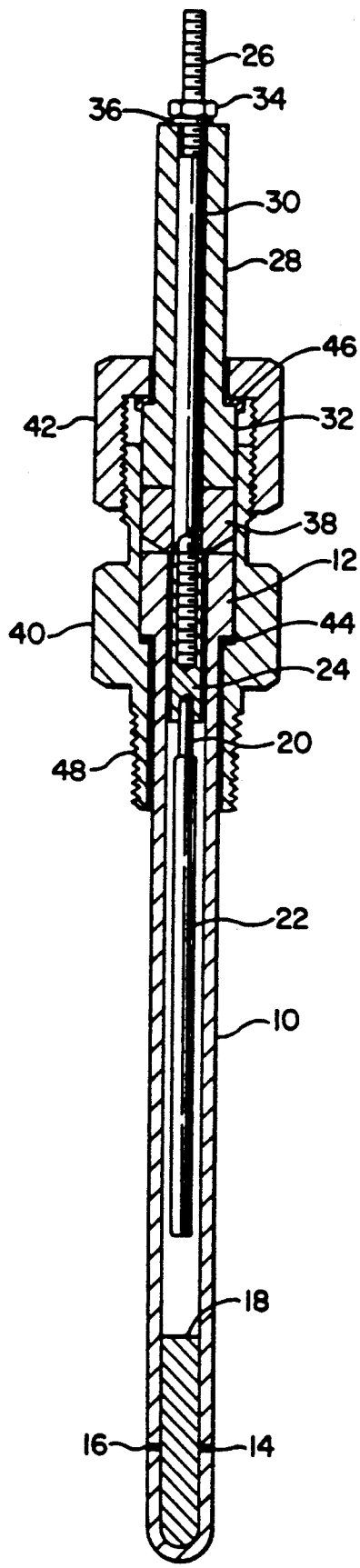
FIG. 1 is a sectional view of a reference Ag/AgCl electrode probe according to the present invention.

Referring specifically to the reference electrode probe depicted at FIG. 1, it will be seen that elongate alumina tube 10 has a closed distal end and an open proximal end terminated by flange 12. Alumina tube 10 is annular in cross-section and is intended to be placed in the water when the probe is employed in monitoring electrochemical potentials. At the distal, closed end of alumina tube 10 are holes 14 and 16 which are 180° apart and currently designed at 0.635 mm (0.025 in) in diameter. The hole diameters, however, may be smaller in size depending upon considerations known to the skilled artisan. Additionally, the number and spacing of holes is left as a variable for the designer of the reference electrode probe.

Quite importantly, zirconia cloth 18 is stuffed into the closed distal end of alumina tube 10 and covers holes 14 and 16. Zirconia is a material that will withstand the high temperature and high pressure environment created within a BWR and is an insulating material, as is the alumina that forms tube 10. Quite importantly, research conducted in connection with development of the inventive reference electrode probe revealed that the zirconia cloth was necessary in order for the probe to exhibit accurate readings within design tolerances over extended periods of time. Without the zirconia cloth, electrochemical potentials measured tend to vary widely, i.e. measurement of ECPs was erratic and the probe unstable in use. Holes 14 and 16 permit water being monitored to flow to within the cavity or annulus created in elongate alumina tube 10. The water also can penetrate to within tube 10 through zirconia cloth 18. Zirconia cloth 18 need not be a woven fabric, but can be discrete fibers packed into the closed distal end of tube 10, as is necessary, desirable, or convenient.

Elongate silver electrode 20 is housed atactilely in, i.e. in spaced-apart relationship from, alumina tube 10 and is coated with silver chloride coating 22. The silver electrode with its silver chloride coating forms the metal/metal ion couple required for the probe to be used as a reference component of an electrode system.

Silver connector 24 also is housed atactilely within alumina tube 10 but at its proximal, flanged open end. Silver connector 24 has a recess at its distal end into which silver electrode 20 is press-fitted. The proximal end of silver connector 24 also contains a recess and is mounted flush with the opening of alumina tube 10. The upper recess at the proximal end of silver connector 24 is threaded for receiving one threaded end of silver alloy rod 26 which is screwed into the threaded proximal recess in silver connector 24. Silver alloy rod 26 preferably is made from coin silver, i.e. silver containing 10 wt-% copper, as pure silver is too soft for use in constructing the rugged-designed inventive probe. Polytetrafluoroethylene (Teflon brand, E. I. DuPont de Nemours and Co., Wilmington, Del.) shrink wrap 30 surrounds silver alloy rod 26 from its distal threaded end to its proximal threaded end. Insulated silver alloy rod 26 is housed within elongate annular alumina insulator 28 which is terminated at its distal end by flange 32. At its proximal end, nut 34 and stainless steel washer 36 retain insulated silver alloy rod 26 firmly against the proximal open end of elongate annular alumina insulator 28.

Disposed between alumina tube 10 and annular alumina insulator 28 is annular elastomeric seal 38 which is tapered at its distal end which is in sealing relationship with the open proximal flanged end of alumina tube 10. The proximal end of elastomeric seal 38 abuts against the distal flanged end of alumina insulator 28.

A threaded two-piece annular high temperature sealing fitting or gland formed of threaded components 40 and 42 contact flanges 12 and 32 with Teflon brand washers 44 and 46 interposed therebetween. When components 40 and 42 are tightened, elastomeric seal 38 forms a water-tight seal against flange 12 of alumina tube 10. Additionally, the annulus of seal 38 sealingly engages shrink wrap 30 about silver alloy rod 26. Finally, the outer circumference of seal 38 is in water-tight sealing engagement against the interior of component 40. Elastomeric seal 38 preferably is formed of polytetrafluoroethylene that has been infiltrated with silica, zirconia, or other similar material in order to reduce expansion and distortion at high temperatures. Threaded connection 48 accommodates installation of the reference electrode through the wall of an enclosure containing an aqueous system in which measurement of ECPs is to be made.

Thus, a water-tight seal of alumina tube 10 has been provided in simple, efficient fashion. The sealing system described is commercially available as EG-125-B-T sealing gland from Conax Corporation (Buffalo, N.Y.). By providing flange 12 on alumina tube 10, a reliable, commercial high temperature sealing gland has been adapted for forming a reference electrode probe that is inexpensive, easy to fabricate, yet has an extremely long shelf life. Such sealing system in combination with a zirconia cloth 18 results in a simple, yet highly efficient reference electrode probe.

Figure 2:
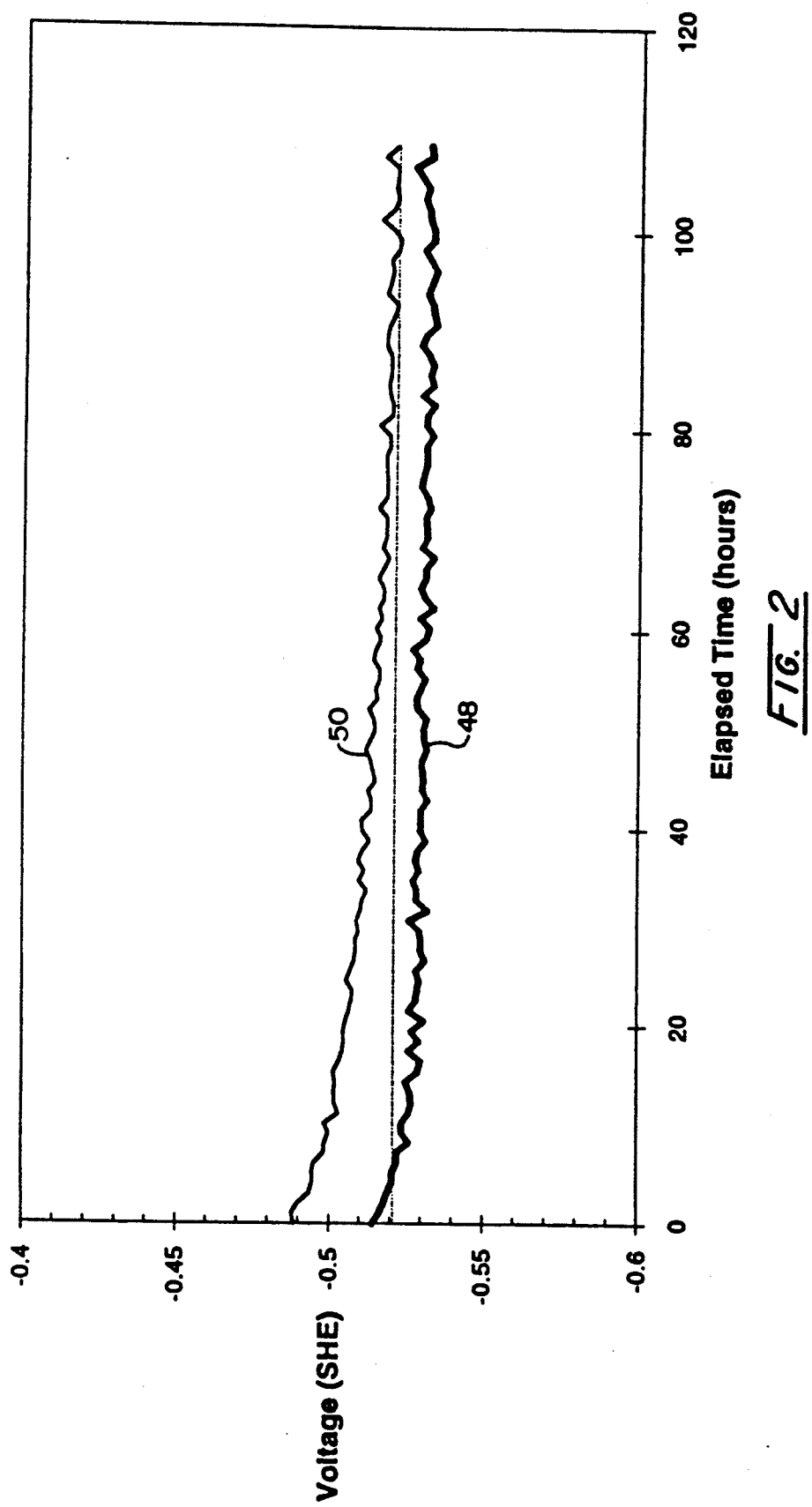
FIG. 2 is a graph showing a laboratory evaluation of two different Ag/AgCl reference electrodes as measured against a standard hydrogen electrode.

Referring to FIG. 2, a sensing platinum electrode probe was subjected to laboratory testing utilizing the inventive reference probe as described herein. The aqueous medium for testing was provided by an autoclave within which the temperature and water chemistry were controlled. The test was carried out at a water temperature of 274° C. The theoretical value that the probes should have read was −0.521 v on the SHE scale. The results of the two novel reference probes are represented at 48 and 50. Not only did the two novel reference electrode probes monitor the desired electrochemical potential within a close tolerance, but their stability and efficiency improved with operational time as can be observed by reference to FIG. 2. Thus, the novel design has been validated.

Since certain changes may be made in the above-described apparatus without departing from the scope of the invention herein involved, it is intended that all matter contained in the description thereof or shown in the accompanying drawings shall be interpreted as illustrative and not in a limiting sense.

We claim:

1. A reference electrode probe for employment in monitoring electrochemical potentials, comprising:
   (a) an elongate alumina tube having a closed distal end and a flanged open proximal end, there being at least one hole penetrating through said tube at its closed distal end;
   (b) an elongate silver electrode coated with silver chloride and housed within said alumina tube in a spaced-apart relationship therefrom;
   (c) fibrous zirconia disposed in the closed distal end of said alumina tube and covering said hole in said alumina tube;
   (d) a silver connector housed within said alumina tube open proximal end in a spaced-apart relationship therefrom, and having a recess at its distal end into which said coated silver electrode is fitted and a recess at its proximal end at the alumina tube opening;
   (e) an insulated silver alloy rod having a distal end fitted into the proximal recess of said silver connector;
   (f) an annular elastomeric seal in sealing relationship with the open proximal end of said alumina tube and retaining in its annulus the distal end of said insulated silver alloy rod;
   (g) an elongate annular alumina insulator having a flanged distal end abutted against the proximal end of said annular seal and retaining said insulated silver alloy rod within its annulus;
   (h) a retainer which retains said insulated silver alloy rod at the proximal end of said annular alumina insulator; and
   (i) a threaded two-piece annular fitting that retains said probe within its annulus and contacts the flange of said alumina tube and the flange of said alumina insulator with polymeric washers interposed between said flanges and said fitting, whereby tightening said fitting brings said annular seal into water-tight sealing relationship with the open proximal end of said alumina tube.

2. The electrode probe of claim 1 wherein said elastomeric seal (f) is formed from polytetrafluoroethylene.

3. The electrode probe of claim 2 wherein said polytetrafluoroethylene seal has been impregnated with silica.

4. The electrode probe of claim 1 wherein said insulated silver alloy rod (e) is made from silver containing about 10 wt-% copper.

5. The electrode probe of claim 1 wherein said insulated silver alloy rod (e) is insulated by a layer of polytetrafluoroethylene.

6. The electrode probe of claim 1 wherein said fibrous zirconia (c) comprises zirconia cloth.

7. The electrode probe of claim 1 wherein the annular fitting includes a distal piece having a threaded outer surface.

8. The electrode probe of claim 1 wherein a pair of diametrically-opposed holes penetrate through said elongate alumina tube.

9. The electrode probe of claim 1 wherein the proximal recess of said silver connector (d) is internally threaded, the distal end of said insulated silver alloy rod (e) is threaded, and said threaded distal end of said insulated silver alloy rod is threaded into the threaded proximal recess of said silver connector.

10. A reference electrode probe for employment in monitoring electrochemical potentials, comprising:
    (a) an elongate alumina tube having a closed distal end and a flanged open proximal end, there being at least one hole penetrating through said tube at its closed distal end;
    (b) an elongate silver electrode coated with silver chloride and housed within said alumina tube in a spaced-apart relationship therefrom;
    (c) zirconia cloth disposed in the closed distal end of said alumina tube and covering said hole in said alumina tube;
    (d) a silver connector housed within said alumina tube open proximal end in a spaced-apart relationship therefrom, and having a recess at its distal end into which said coated silver electrode is fitted and a recess at its proximal end at the alumina tube opening;
    (e) an insulated silver alloy rod having a distal end fitted into the proximal recess of said silver connector, said rod made from silver containing about 10 wt-% copper;
    (f) an annular elastomeric seal in sealing relationship with the open proximal end of said alumina tube and retaining in its annulus the distal end of said insulated silver alloy rod, said seal made from polytetrafluoroethylene impregnated with silica;
    (g) an elongate annular alumina insulator having a flanged distal end abutted against the proximal end of said annular seal and retaining said insulated silver alloy rod within its annulus;
    (h) a retainer which retains said insulated silver alloy rod at the proximal end of said annular alumina insulator; and
    (i) a threaded two-piece annular fitting that retains said probe within its annulus and contacts the flange of said alumina tube and the flange of said alumina insulator with polymeric washers interposed between said flanges and said fitting, whereby tightening said fitting brings said annular seal into water-tight sealing relationship with the open proximal end of said alumina tube.

11. The electrode probe of claim 10 wherein said zirconia cloth extends up to and contacts said silver electrode.

12. The electrode probe of 10 wherein said zirconia cloth extends up to but is spaced-apart from said silver electrode.

13. The electrode probe of claim 10 wherein a pair of diametrically-opposed holes penetrate through said elongated alumina tube.

14. The electrode probe of claim 13 wherein the proximal recess of said silver connector (d) is internally threaded, the distal end of said insulated silver alloy rod (e) is threaded, and said threaded distal end of said insulated silver alloy rod is threaded into the threaded proximal recess of said silver connector.

15. The electrode probe of claim 10 wherein the proximal recess of said silver connector (d) is internally threaded, the distal end of said insulated silver alloy rod (e) is threaded, and said threaded distal end of said insulated silver alloy rod is threaded into the threaded proximal recess of said silver connector.

* * * * *